(12) United States Patent
Schwartz et al.

(10) Patent No.: US 7,947,510 B2
(45) Date of Patent: May 24, 2011

(54) METHODS AND DEVICES FOR DETECTING NUCLEIC ACID HYBRIDIZATION

(75) Inventors: Daniel K. Schwartz, Boulder, CO (US); Andrew D. Price, Nederland, CO (US)

(73) Assignee: The Regents of the University of Colorado, a body corporate, Denver, CO (US)

( * ) Notice: Subject to any disclaimer, the term of this patent is extended or adjusted under 35 U.S.C. 154(b) by 0 days.

(21) Appl. No.: 12/185,008

(22) Filed: Aug. 1, 2008

(65) Prior Publication Data

US 2009/0061527 A1 Mar. 5, 2009

Related U.S. Application Data

(60) Provisional application No. 60/953,887, filed on Aug. 3, 2007.

(51) Int. Cl.
*G01N 21/00* (2006.01)
(52) U.S. Cl. ......... 436/164; 436/94; 435/287.1; 349/56; 349/61; 349/167; 349/199
(58) Field of Classification Search .................. None
See application file for complete search history.

(56) References Cited

OTHER PUBLICATIONS

Ramakrishnan, Vidya, et al. Effect of salt on the hybridization of DNA by sequential immobilization of oligonucleotides at the air-water interface on the presence of ODA/DOTAP monolayers, 2004, Journal of Colloid and Interface Science, vol. 276, pp. 77-84.*
Brake, J.M. et al., Formation and characterization of phospholipid monolayers spontaneously assembled at interfaces between aqueous phases and thermotropic liquid crystals, Langmuir, 21(6):2218-2228, 2005, downloaded from http://pubs.acs.org on Apr. 14, 2009.
Brake, J.M. et al., Coupling of the orientations of thermotropic liquid crystals to protein binding events at lipid-decorated interfaces, Langmuir, 23(16):8497-507, 2007, downloaded from http://pubs.acs.org on Apr. 14, 2009.
Brake, J.M. et al., Biomolecular interactions at phospholipid-decorated surfaces of liquid crystals, Science, 302:2094-97, 2003, downloaded from www.sciencemag.org on Apr. 14, 2009.
Brake, J.M. et al., Effect of surfactant structure on the orientation of liquid crystals at aqueous-liquid crystal interfaces, Langmuir, 19(16):6436-42, 2003, downloaded from http://pubs.acs.org on Apr. 14, 2009.
Cardenas, M. et al., The interaction between DNA and cationic lipid films at the air-water interface, Journal of Colloid and Interface Science, 286:166-75, 2005.
Chen, X., et al., Influence of surfactant molecular structure on two-dimensional surfactant-DNA complexes: Langmuir balance study, Journal of Colloid and Interface Science, 287:185-90, 2005.
Clare, B.H. et al., Orientations of nematic liquid crystals on surfaces presenting controlled densities of peptides: amplification of protein-peptide binding events, Langmuir, 21(14)6451-61, 2005, downloaded from http://pubs.acs.org on Apr. 14, 2009.
Erokhina, S. et al., Interaction of DNA oligomers with cationic lipidic monolayers: complexation and splitting, Langmuir, 23:4414-20, 2007.
Gupta, V.K. et al., Optical amplification of ligand-receptor binding using liquid crystals, Science, 279:2077-80, 1998, downloaded from www.sciencemag.org on Apr. 14, 2009.

(Continued)

*Primary Examiner* — Yelena G Gakh
*Assistant Examiner* — Robert Xu
(74) *Attorney, Agent, or Firm* — Don D. Cha; Hamilton DeSanctis & Cha, LLP

(57) ABSTRACT

The present invention provides novel methods and devices for detecting hybridization of nucleic acids using liquid crystals and cationic surfactants.

12 Claims, 8 Drawing Sheets

OTHER PUBLICATIONS

Kago, K. et al., Direct in Situ observation of a lipid monolayer-DNA complex at the air-water interface by x-ray reflectometry, Langmuir, 15(16):5193-96, 1999, downloaded from http://pubs.acs.org on Apr. 14, 2009.

Kim, H.-R. et al., Optical detection of deoxyribonucleic acid hybridization using an anchoring transition of liquid crystal alignment, Appl. Phys. Lett., 87:143901, 3 pgs., 2005.

Kim, S.-R. et al., Manipulation of the orientational response of liquid crystals to proteins specifically bound to covalently immobilized and mechanically sheared films of functionalized bovine serum albumin, Langmuir, 18(13):5269-5276, 2002, downloaded from http://pubs.acs.org on Apr. 14, 2009.

Koltover, I. et al., An inverted hexagonal phase of cationic liposome-DNA complexes related to DNA release and delivery, Science, 281:78-81, 1998, downloaded from www.sciencemag.org on Apr. 14, 2009.

Luk, Y.-Y. et al., Using liquid crystals to amplify protein-receptor interactions: design of surfaces with nanometer-scale topography that present histidine-tagged protein receptors, Langmuir, 19(5):1671-80, 2003, downloaded from http://pubs.acs.org on Apr. 14, 2009.

Park, J.-S. et al., Formation of oligopeptide-based polymeric membranes at interfaces between aqueous phases and thermotropic liquid crystals, Chem. Mater., 18(26):6147-51, 2006, downloaded from http://pubs.acs.org on Apr. 14, 2009.

Price, A.D. et al., Fatty-acid monolayers at the nematic/water interface: phases and liquid-crystal, J. Phys. Chem. B, 111(5):1007-15, 2007, downloaded from http://pubs.acs.org on Apr. 14, 2009.

Radler, J.O, et al., Structure of DNA-cationic liposome complexes: DNA intercalation in multilamellar membranes in distinct interhelical packing regimes, Science, 275:810-814, 1997, downloaded from www.sciencemag.org on Apr. 14, 2009.

Ramakrishnan, Y. et al., Effect of salt on the hybridization of DNA by sequential immobilization of oligonucleotides at the air-water interface in the presence of ODA/DOTAP monolayers, Journal of Colloid and Interface Science, 276:77-84, 2004.

Sastry, M. et al., Hybridization of DNA by sequential immobilization of oligonucleotides at the air-water interface, Langmuir, 16(24):9142-46, 2000, downloaded from http://pubs.acs.org on Apr. 14, 2009.

Symietz, C. et al., DNA alignment at cationic lipid monolayers at the air/water interface, Macromolecules, 37(10):3865-73, 2004, downloaded from http://pubs.acs.org on Apr. 14, 2009.

* cited by examiner

SEQUENCE LISTING

```
<160> NUMBER OF SEQ ID NOS: 5

<210> SEQ ID NO 1
<211> LENGTH: 16
<212> TYPE: DNA
<213> ORGANISM: Artificial Sequence
<220> FEATURE:
<223> OTHER INFORMATION: Synthetic construct - 16mer ssDNA
      oligonucleotide

<400> SEQUENCE: 1
agaaaaaact tcgtgc                                                  16

<210> SEQ ID NO 2
<211> LENGTH: 16
<212> TYPE: DNA
<213> ORGANISM: Artificial Sequence
<220> FEATURE:
<223> OTHER INFORMATION: Synthetic construct - 16mer target
      oligonucleotide

<400> SEQUENCE: 2
gcacgaagtt ttttct                                                  16

<210> SEQ ID NO 3
<211> LENGTH: 16
<212> TYPE: DNA
<213> ORGANISM: Artificial Sequence
<220> FEATURE:
<223> OTHER INFORMATION: Synthetic construct - 16mer oligonucleotide

<400> SEQUENCE: 3
gggcggatga gtcagt                                                  16

<210> SEQ ID NO 4
<211> LENGTH: 16
<212> TYPE: DNA
<213> ORGANISM: Artificial Sequence
<220> FEATURE:
<223> OTHER INFORMATION: Synthetic construct - 16mer oligonucleotide

<400> SEQUENCE: 4
gcaggaagtt tattct                                                  16
```

```
<210> SEQ ID NO 5
<211> LENGTH: 16
<212> TYPE: DNA
<213> ORGANISM: Artificial Sequence
<220> FEATURE:
<223> OTHER INFORMATION: Synthetic construct - 16mer oligonucleotide

<400> SEQUENCE: 5
gcacgaactt ttttct                                                        16
```

METHODS AND DEVICES FOR DETECTING NUCLEIC ACID HYBRIDIZATION

CROSS-REFERENCES TO RELATED APPLICATIONS

This application claims the benefit of U.S. Provisional Patent Application No. 60/953,887, filed Aug. 3, 2007, the contents of which is herein incorporated by reference in its entirety for all purposes.

STATEMENT AS TO RIGHTS TO INVENTIONS MADE UNDER FEDERALLY SPONSORED RESEARCH OR DEVELOPMENT

The invention was made with government support under grant number DMR-0213918 awarded by the National Science Foundation. The government has certain rights in the invention.

BACKGROUND OF THE INVENTION

Thermotropic liquid crystals (LC) have demonstrated utility in the transduction of molecular events at an interface into macroscopic responses visible with the naked eye (Brake et al., 2007; Park et al., 2006; Clare et al., 2005; Kim et al., 2005; Brake et al., 2003; Luk et al., 2003; Kim et al., 2002; Gupta et al., 1998). The orientation of LC molecules is extraordinarily sensitive to physical and chemical properties of a bounding interface, and the long-range order inherent in LC phases serves to amplify surface-induced ordering for macroscopic distances. These properties, combined with the optical anisotropy of LC molecules make them well-suited for the direct transduction and amplification of the binding of an analyte to a target at an interface into an optical output (Hoogboom et al., 2003). Unlike most current methods for the detection of biological analytes, which generally require laboratory-based analytical detectors and labeled species such as fluorophores or radioactive isotopes (Blum et al., 1991), LC-based detection may be carried out in ambient light without the need for electrical power or molecular labels. This makes LC-based detection particularly useful for detection assays performed away from central laboratory locations including point-of-care, home-based, and field-based assays.

Principles of LC-based detection rely on optical, anchoring, and elastic properties arising from molecular anisotropies and the unique liquid-crystalline phase of the LC material (de Gennes et al., 1995). The molecular anisotropy of a liquid crystalline sample creates a difference in the refractive indices of light parallel and perpendicular to the bulk molecular orientation, i.e. the LC director (Dunmur et al., 2001). This difference, known as birefringence, creates a discernable optical signal that is lost when the director orients parallel to the direction of light propagation. Molecular-scale interactions between a LC and a neighboring interface result in a preferred anchoring angle relative to the surface normal (Rasing et al., 2004). Information about the interface, in the form of surface anchoring, is transmitted as far as 100 µm into the bulk (Gupta et al., 1998) as a result of the elastic nature of the LC director field.

Coupling the structure of the interface to a bioreaction, such as molecular recognition, may cause a bulk reorientation of the LCs as the reaction proceeds, generating an optical signal. The aqueous/LC interface is particularly interesting in this regard, because the aqueous phase permits convenient molecular transport to the interface and the fluidity of the interface allows for large-scale molecular re-arrangements. Furthermore, the chemical properties of the interface can be modified in a controlled way by adsorption of a surfactant monolayer (Price et al., 2007; Lockwood et al., 2005). In the absence of surfactant, a highly tilted (nearly planar) LC orientation is observed. At sufficient surfactant coverage, the tilted anchoring at the interface reorients to a homeotropic alignment (Price et al., 2007; Brake et al., 2005). We have previously shown that long-chain n-alkanoic acids adsorbed at the aqueous/LC interface possess distinct 2D phases dependent on the surfactant chemical potential and the temperature of the interface (Price et al., 2007). These phases are also characterized by molecular packing density, tilt, and lateral organization (Kaganer et al., 1999). LC anchoring is sensitive to these structural details (Brake et al., 2003).

Deoxyribonucleic acid (DNA) has long been known to form insoluble complexes with cationic surfactants in aqueous environments (Osica et al., 1997). In some cases, the complexes form highly-ordered lamellar structures, with DNA intercalated into surfactant bilayers (Radler et al., 1997). Research into DNA-lipid complexes has been predominantly driven by expectations of their use as nonviral gene carriers in transfection applications (Radler et al., 1997; Koltover et al., 1998; Miller, 1998) and in molecular diagnostics (Sastry, et al., 2000). Despite the promise of DNA/lipid complexes, DNA interactions with charged surfaces remain poorly understood (Erokhina et al., 2007). The use of Langmuir monolayers of cationic lipids has provided one method for probing DNA at such surfaces (Sastry et al., 2000; Erokhina et al., 2007; Sukhorukov et al., 1996; Kaganer et al., 1999; Ramakrishnan et al., 2004; Symietz et al., 2004; Cardenas et al., 2005; Chen et al., 2005). Möhwald et al. have shown that DNA binding to a cationic phospholipid monolayer condenses the membrane surface (Symietz et al., 2004). Furthermore, Sastry et al. measured molecular area changes upon hybridization of an oligomer target to membrane-bound DNA probes at the air/water interface (Sastry et al., 2000; Rmamkrishnan et al., 2004) and Sukhorukov et al. showed that double-stranded DNA (dsDNA) does not denature upon adsorbing to a cationic surfactant monolayer at a similar interface (Sukhorukov et al., 1996).

To date, there exists no successful method to detect nucleic acid hybridization using liquid crystals and a cationic surfactant interface. The present invention solves this and other problems in the art.

SUMMARY OF THE INVENTION

It has been discovered that liquid crystals and cationic surfactants may be used to accurately and sensitively detect hybridization of nucleic acids. In some embodiments, the methods and devices are suitable for practicing in the field and do not require a power source, thereby providing a more convenient and portable system than prior methods and devices. Thus, the methods and devices disclosed herein provide a cost effective means for detecting hybridization of nucleic acids.

In one aspect, the present invention provides a method of detecting hybridization of a probe nucleic acid and a sample nucleic acid. The method includes contacting a sample nucleic with a cationic surfactant-nucleic acid interfacial layer. The cationic surfactant-nucleic acid interfacial layer comprises a cationic surfactant and a probe nucleic acid. The cationic surfactant-nucleic acid interfacial layer is present at the interface of a liquid crystal and a polar solvent. The sample nucleic acid is allowed to hybridize to the probe nucleic acid thereby reorienting the liquid crystal. The reorienting is detected thereby detecting hybridization of the probe nucleic acid to the sample nucleic acid.

In another aspect, the invention provides a device to detect nucleic acid hybridization on a solid substrate. The device includes a solid substrate, a liquid crystal, a polar solvent, and a cationic surfactant-nucleic acid interfacial layer. In some embodiments, the liquid crystal is in contact with (e.g. on top of) the solid substrate. In other embodiments, the polar solvent is in contact with (e.g. on top of) the solid substrate. The cationic surfactant-nucleic acid interfacial layer comprises a cationic surfactant and a probe nucleic acid. The cationic surfactant-nucleic acid interfacial layer is present at the interface of the liquid crystal and the polar solvent.

In another aspect, the invention provides a kit to detect nucleic acid hybridization. The kit includes a liquid crystal, and a cationic surfactant, and probe nucleic acid dissolved in a polar solvent. In some embodiments, the kit further includes a solid substrate.

DETAILED DESCRIPTION OF THE INVENTION

I. Definitions

Figure 1:
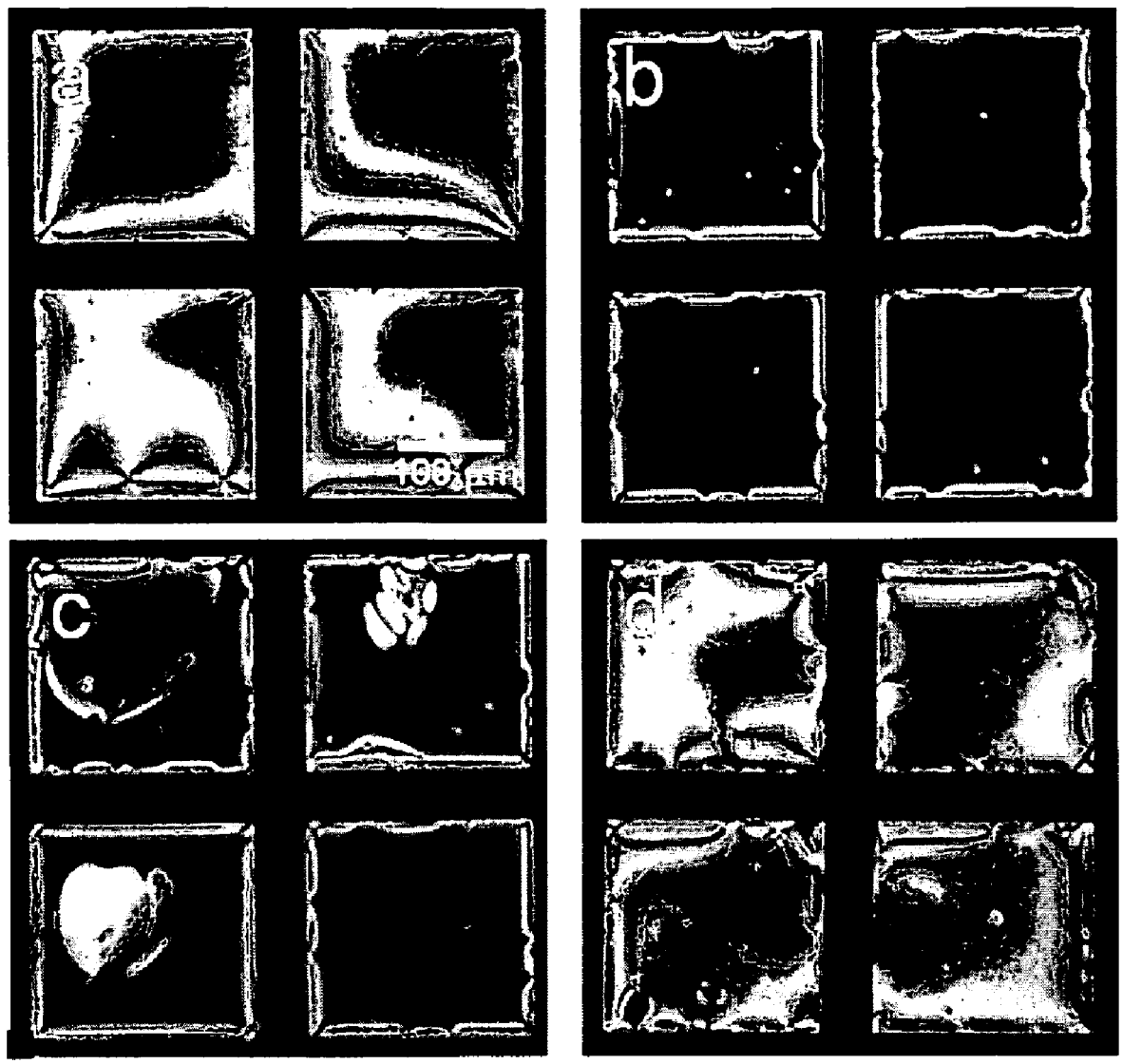
FIG. 1 (a) illustrates the self-assembly of an OTAB layer at the LC/aqueous interface and how it causes homeotropic alignment of the LC layer; (b) Birefringent regions appear upon exposure of the layer to a ssDNA probe; (c) Birefringent regions expand until the holes are predominately birefringent; (d) LC appearance in the absence of an OTAB layer when in contact with water.

As used herein, "nucleic acid" means single stranded DNA, RNA and derivative thereof. Modifications include, but are not limited to, those which provide other chemical groups that incorporate additional charge, polarizability, hydrogen bonding, electrostatic interaction, and functionality to the nucleic acid ligand bases or to the nucleic acid ligand as a whole. Such modifications include, but are not limited to, phosphodiester group modifications (e.g., phosphorothioates, phosphorodithioates, boranophosphonates, methylphosphonates), 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, methylations, unusual base-pairing combinations such as the isobases isocytidine and isoguanidine and the like. Modifications can also include 3' and 5' modifications such as capping moieties. A 2'deoxy nucleic acid linker is a divalent nucleic acid compound of any appropriate length and/or internucleotide linkage wherein the nucleotides are 2'deoxy nucleotides. A "sample nucleic acid" is a nucleic acid to be tested to determine whether hybridization occurs with a probe nucleic acid, wherein the sequence of the probe nucleic acid is typically known.

A "nucleobase" refers to the portion(s) of a nucleic acid involved in hybridization (base pairing), and includes, but is not limited to, nitrogenous bases such as cytosine, guanine, adenine, thymine, uracil, and derivatives thereof.

The term "hybridization" refers to the pairing of complementary strands of nucleic acids, including triple-stranded nucleic acid hybridization. The mechanism of pairing involves hydrogen bonding, which may be Watson-Crick, Hoogsteen or reversed Hoogsteen hydrogen bonding, between complementary nucleoside or nucleotide bases (nucleobases) of the strands of nucleic acids. For example, adenine and thymine are complementary nucleobases that pair through the formation of hydrogen bonds. Hybridization can occur under varying circumstances.

The term "stringent hybridization conditions" or "stringent conditions" refers to conditions under which a nucleic acid hybridizes to form a stable complex (e.g. a duplex) with its complement, but to a minimal number of other sequences. The stability of the complex is a function of salt concentration and temperature (See, for example, Sambrook et al., Molecular Cloning: A Laboratory Manual 2d Ed. (Cold Spring Harbor Laboratory, (1989); incorporated herein by reference). Stringency levels used to hybridize nucleic acids can be readily varied by those of skill in the art.

"Complementary," as used herein, refers to the capacity for precise pairing of two nucleobases (e.g. A to T (or U), and G to C) regardless of where in the nucleic acid the two are located. For example, if a nucleobase at a certain position of nucleic acid is capable of hydrogen bonding with a nucleobase at a certain position of another nucleic acid, then the position of hydrogen bonding between the two nucleic acids is considered to be a complementary position. Nucleic acids are "substantially complementary" to each other when a sufficient number of complementary positions in each molecule are occupied by nucleobases that can hydrogen bond with each other. Thus, the term "substantially complementary" is used to indicate a sufficient degree of precise pairing over a sufficient number of nucleobases such that stable and specific binding occurs between the nucleic acids. The phrase "substantially complementary" thus means that there may be one or more mismatches between the nucleic acids when they are aligned, provided that stable and specific binding occurs. The term "mismatch" refers to a site at which a nucleobase in one nucleic acid and a nucleobase in another nucleic acid with which it is aligned are not complementary. The nucleic acids are "perfectly complementary" to each other when they are fully complementary across their entire length.

Generally, a nucleic acid is "antisense" to another nucleic acid when, written in the 5' to 3' direction, it comprises the reverse complement of the corresponding region of the target nucleic acid. "Antisense compounds" are also often defined in the art to comprise the further limitation of, once hybridized to a target, being able to modulate levels, expression or function of the target compound.

As used herein, "sequence identity" or "identity" refers to the nucleobases in two sequences that are the same when aligned for maximum correspondence over a specified comparison window. As used herein, "percentage of sequence identity" means the value determined by comparing two optimally aligned sequences over a comparison window, wherein the portion of the sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

II. Methods and Devices

In one aspect, the present invention provides a method of detecting hybridization of a probe nucleic acid and a sample nucleic acid. The method includes contacting a sample nucleic with a cationic surfactant-nucleic acid interfacial layer. The cationic surfactant-nucleic acid interfacial layer comprises a cationic surfactant and a probe nucleic acid. The cationic surfactant-nucleic acid interfacial layer is present at the interface of a liquid crystal and a polar solvent. The sample nucleic acid is allowed to hybridize to the probe nucleic acid thereby reorienting the liquid crystal. The reorienting is detected thereby detecting hybridization of the probe nucleic acid to the sample nucleic acid. The cationic surfactant-nucleic acid interfacial layer may be formed by combining a cationic surfactant, a liquid crystal, and a probe nucleic acid dissolved in a polar solvent.

The sample nucleic acid and the probe nucleic acid are typically dissolved in a polar solvent, such as an aqueous solution (e.g. water). The nucleic acid in its polar solvent is exposed to the liquid crystal. In some embodiments, the liquid crystal contains the cationic surfactant at the time the polar solvent contacts the liquid crystal. In other embodiments, the cationic surfactant is dissolved in the polar solvent with probe nucleic acid prior to contacting the liquid crystal with the polar solvent. And in still other embodiments, the cationic surfactant is added to an interface formed between the polar solvent and the liquid crystal. Without being bound by any particular mechanistic theory, it is believed that the cationic surfactant forms a cationic surfactant layer (e.g. a cationic surfactant monolayer) at the interface between the liquid crystal and aqueous solutions, and that hybridization occurs at the interface between the liquid crystal and aqueous solutions. The cationic surfactant monolayer may interact with (or complex with) the probe nucleic acid through its cationic headgroups.

Formation of the cationic surfactant-nucleic acid interfacial layer is typically a spontaneous reaction which occurs when a cationic surfactant is combined with the liquid crystal and the polar solvent (such as water) containing the probe nucleic acid. In some embodiments, the result is a closed-packed alignment of cationic headgroups that interact with an anionic binding partners (e.g. phosphate backbone of nucleic acids). In some embodiments, the cationic surfactant is a monoalkyl quaternary ammonium salt surfactant, a dialkyl quaternary ammonium salt surfactant, a trialkyl quaternary ammonium salt surfactant, or a monoalkylpyridinium salt surfactant. Examples of monoalkyl quaternary ammonium salt surfactants include monoalkyl quaternary ammonium bromide and chloride salts such as dodecyltrimethylammonium bromide, dodecyltrimethylammonium chloride, tetradecyltrimethylammonium bromide, tetradecyltrimethylammonium chloride, hexadecyltrimethylammonium bromide, or hexadecyltrimethylammonium chloride. In some embodiments, the monoalkyl quaternary ammonium salt surfactant is octadecyltrimethylammonium bromide (OTAB).

In other embodiments, the cationic surfactant is a dialkyl quaternary ammonium surfactant, such as dioctadecyldimethylammonium bromide. The cationic surfactant may also be a trialkyl quaternary ammonium salt surfactant such as trioctadecylmethylammonium bromide. And in certain embodiments, the cationic surfactant is a monoalkylpyridinium salt surfactant, such as hexadecylpyridinium bromide.

As described above, the cationic surfactant may be dissolved in a liquid crystal and incubated (e.g. contacted) to an aqueous phase containing the probe nucleic acid thereby forming a cationic surfactant-nucleic acid interfacial layer at the liquid crystal/aqueous interface. In some embodiments, the cationic surfactant and probe nucleic acid form a cationic surfactant-nucleic acid complex (i.e. a non-covalent association). The cationic surfactant-nucleic acid complex is exposed to a sample nucleic acid resulting in hybridization of the probe nucleic acid portion of the cationic surfactant-nucleic acid complex with the sample nucleic acid. Hybridization of the cationic probe nucleic acid and the sample nucleic acid induces a reorientation of the liquid crystal which is detectable and indicative of the hybridization between the probe nucleic acid and the sample nucleic acid.

In some embodiments, the nucleic acid is DNA or RNA. The DNA or RNA may be synthetic or derived from a cell or organism (e.g. genomic). In some embodiments, the probe nucleic acid is 5 to 50 nucleobases in length. In other embodiments, the probe nucleic acid is 20 to 30 nucleobases long. The sample nucleic acid may be of any appropriate length, and hybridizes to the probe nucleic acid when sufficiently complementary. The ability of the sample nucleic acid to hybridize to the probe nucleic acid may be controlled at least in part by adjusting environmental factors such as temperature, salt concentration, the concentration of probe nucleic acid and/or sample nucleic acid, the length of the probe nucleic acid and/or sample nucleic acid, and the presence and/or concentration of denaturants. Thus, in some embodiments, the sample nucleic acid hybridizes to the probe nucleic acid where the sample nucleic acid contains from 1 to 5 nucleobase mismatches. In other embodiments, the sample nucleic acid hybridizes to the probe nucleic acid where the sample nucleic acid is substantially complementary or perfectly complementary to the probe nucleic acid. In some embodiments, the sample nucleic acid has 70%, 80%, 90%, 95%, 96%, 97%, 98%, 99%, or 100% sequence identity with the probe nucleic acid. The sample nucleic acid may also be antisense to the probe nucleic acid.

In some embodiments, the liquid crystal is a thermotropic liquid crystal, a polymeric liquid crystals, nematic liquid crystal, smectic liquid crystal, columnar liquid crystal, nematic discotic liquid crystal, calamitic liquid crystal, ferroelectric liquid crystal, discoid liquid crystal, cholesteric liquid crystal or mixtures thereof. In certain embodiments, the liquid crystal is a thermotropic liquid crystals. The thermotropic liquid crystal may include 5CB (4-cyano-4'-pentylbiphenyl), 5 CT (4-Cyano-4'-pentyl-p-terphenyl), MBBA (N-(4-methoxybenzylidene-4'-butylaniline), 4,4'-Di-n-hexyldiphenyldiacetylene, or a mixture thereof. In certain embodiments, the liquid crystal is E7. The liquid crystal is typically hydrophobic and therefore capable of forming a layer separated from a polar solvent. Thus, in some embodiments, the liquid crystal is a liquid crystal layer. The cationic surfactant-nucleic acid interfacial layer may form on top of the liquid crystal layer. A polar solvent layer may reside above the cationic surfactant-nucleic acid interfacial layer. In other embodiments, the cationic surfactant-nucleic acid interfacial layer may form on top of the polar solvent layer and below the liquid crystal layer.

In some embodiments, the reorientation (also referred to herein as a phase transition, second phase transition, or 2D phase separation) of the liquid crystal is detected by measuring changes in the birefringence of the liquid crystal. Again, without being bound by any particular mechanistic theory, it is believed that the interaction between the interfacial probe nucleic acid and the sample nucleic acid at the interface between liquid crystal and polar solvent induces a phase change in the cationic surfactant-nucleic acid interfacial layer which then causes a reorientation of the liquid crystal. The reorientation of the liquid crystal changes the direction of the birefringent optical axes of the liquid crystal material relative to the direction of the propagation of light through the device. This changes the effective birefringence of the device and creates a discernable optical signal.

The reorientation and birefringence of the liquid crystal described herein may be monitored using any appropriate technique known to those of skill in the art, such as polarized light microscopy. Liquid crystal orientation and textures may be observed with a light microscope that has been modified for transmission mode incorporating crossed polarizers. In some embodiments, the changes in birefringence are detected with the naked eye using a light source and two polarizers, such as in a passive LCD display.

In other embodiments, the reorientation may be detected by detecting changes to the optical texture of the liquid crystal upon hybridization of the probe nucleic acid and sample nucleic acid.

In some embodiments, the methods may be used to determine the hybridization of a plurality of probe nucleic acids to one or more sample nucleic acids. Thus, the methods of the present invention may include more than one probe nucleic acid and/or more than one sample nucleic acid.

In another aspect, the invention provides a device to detect nucleic acid hybridization. The device includes a solid substrate, a liquid crystal on the solid substrate, a polar solvent, and a cationic surfactant-nucleic acid interfacial layer. The solid substrate functions to support the liquid crystal and/or the polar solvent depending upon the particular orientation as described in the methods above. The cationic surfactant-nucleic acid interfacial layer comprises a cationic surfactant and a probe nucleic acid. The cationic surfactant-nucleic acid interfacial layer is present at the interface of the liquid crystal and the polar solvent. In some embodiments, the devise further includes a sample nucleic acid hybridized to the probe nucleic acid. The solid substrate is typically selected to be non-reactive with the liquid crystal, the cationic surfactant, and/or the nucleic acids. The solid substrate is also typically substantially planar to provide a surface support for the liquid crystal.

In some embodiments, the device is in the form of a multiplex device in an array format such as a biochip. The multiplex device may include a plurality of liquid crystals separated or compartmentalized in an array format, in which each liquid crystal compartment includes a cationic surfactant-nucleic acid interfacial layer and a different probe nucleic acid sequence. Thus, the multiplex device is capable of hybridizing a plurality of different sample nucleic acids to a plurality of different probe nucleic acids.

In another aspect, the invention provides a kit to detect nucleic acid hybridization. The kit includes a liquid crystal, and a cationic surfactant, and probe nucleic acid dissolved in a polar solvent. The kit may also include a solid substrate (e.g. a biochip) and/or a sample nucleic acid.

In another aspect, the invention provides a cationic surfactant-nucleic acid interfacial layer formed by combining a cationic surfactant, a liquid crystal, and a nucleic acid in a polar solvent. In another aspect, the invention provides a cationic surfactant-nucleic acid interfacial layer. The cationic surfactant-nucleic acid interfacial layer comprises a cationic surfactant and a probe nucleic acid. The cationic surfactant-nucleic acid interfacial layer is present at the interface of (e.g. between) the liquid crystal and the polar solvent.

The elements of the methods disclosed herein are equally applicable, where appropriate, to the disclosed compositions and devices. For example, the characteristics of the cationic surfactant-nucleic acid interfacial layer described in the description of the methods herein are equally applicable to the cationic surfactant-nucleic acid interfacial layer referred to in the description of the devices, kits, and compositions.

EXAMPLES

The following examples are meant to illustrate certain embodiments of the invention, and not to limit the scope of the inventions disclosed herein.

Materials

LC Film Preparation: Borosilicate glass slides were cleaned with a fresh piranha solution composed of 30% aqueous $H_2O_2$ and concentrated $H_2SO_4$ (1:3 v/v) for 1 h at 70° C. An octadecyltriethoxysilane (OTES) (Gelest, Inc.) self-assembled monolayer (SAM) was deposited on the glass following the procedure described by Walba et al. Briefly, clean glass slides were rinsed with acetone and toluene and submerged in a solution of toluene, OTES, and butylamine (200:3:1 v/v) for 30 min at 60° C. Following, the glass slides were rinsed with toluene, dried with a stream of nitrogen, and stored under a vacuum at room temperature for 24 h prior to use. This produced a surface with a water contact angle ~95° as measured optically by the sessile drop method with a goniometer; sufficient to induce homeotropic alignment of the liquid crystal (LC). The slides were cut into small rectangles measuring approximately 0.25×0.20 in.

The LC material used was E7 ($n_\perp$=1.57, $n_\parallel$=1.73, Merck Ltd.), a four-component LC mixture of cyanobiphenyls and a cyanoterphenyl with a nematic to isotropic (N-I) transition temperature of 60° C. (Dunmur et al., 2001). Octadecylammonium bromide (OTAB, Aldrich) dissolved in chloroform was added to the LC material, briefly mixed with a glass pipette, then dried under a stream of nitrogen. The final concentration of OTAB in the LC was 100±20 µM. The LC was drawn into a 25 µm capillary tube and used to fill a gilded TEM grid via capillary action by contacting the capillary tube to the grid laying flat on a rectangle of SAM-coated glass. The TEM grid (SPI Supplies) used was a gold-coated copper, square mesh grid with hole sizes of 205 µm. Following the introduction of the LC into the grid, the LC was heated above its nematic-to-isotropic transition temperature and slowly cooled back to room temperature. This resulted in a LC layer of approximately 20 µm in thickness.

Adsorption of ssDNA: Eight-well chamber slides (Lab-Tek) were filled with 500 μl of a solution consisting of 5 mM sodium chloride, 2.5 μM of 16 mer single-stranded DNA (ssDNA) oligonucleotides, AGAAAAAACTTCGTGC, (SEQ ID NO:1) (Operon), henceforth called sequence A, and up to 10% formamide, if used. The pH of this solution ranged from 5.5-6.0. LC-filled TEM grids on SAM-coated glass were submerged in the solution for 30-60 minutes, sufficient time for an OTAB/ssDNA monolayer at the LC/aqueous interface to reach a steady-state surface coverage. The solution was held constant at 25° C. throughout the formation of the monolayer. A cover was placed on the chamber to limit evaporation.

Polarized Light Microscopy: The LC orientation and textures were observed using plane-polarized light with an Olympus microscope (model BH2-UMA) modified for transmission mode incorporating crossed polarizers. The chamber slide containing the LC setup was placed on a rotating stage with an attached custom, liquid-based heating and cooling stage. The stage was located between the polarizers. All images were captured using a Lumenera (model Infinity 1-C) digital video camera mounted on the microscope and positioned so its x and y axes were aligned with those of the polarizer and analyzer. The 5× magnification was provided by an Olympus objective with plan-achromat design, a numerical aperature (NA), of 0.13 and working distance of 18.0 mm. Images were captured using Lumenera's Infinity Capture software. Homeotropic orientation was determined by the absence of transmitted light during a full 360° rotation of the sample. An image analysis program, ImageJ, was used to measure homeotropic coverage in the holes of the TEM grid. In the absence of homeotropic orientation, zenithal tilt angle at the nematic/water interface was determined by comparing the observed colors to those on a Michel-Levy chart (Robinson et al., 2006). This yielded the birefringence, from which we were then able to determine $\theta_{n/w}$ the zenithal angle of the LC director at the nematic/water interface, from the following equation:

$$\Delta n_e = \frac{1}{\theta_{n/w} - \theta_{n/SAM}} \int_{\theta_{n/SAM}}^{\theta_{n/a}} \frac{n_\| n_\perp \, d\theta}{\sqrt{n_\|^2 \cos^2\theta + n_\perp^2 \sin^2\theta}} - n_\perp$$

where $\Delta n_e$ was the effective average birefringence, $n_\|$ was the index of refraction for E7 parallel to the optical axis, and $n_\perp$ was the index of refraction for E7 perpendicular to the optical axis. $\theta_{n/SAM}$ was the zenithal angle of the LC director at the nematic/SAM interface and was assumed to always have a value of 0 (homeotropic anchoring). The azimuthal angle was determined by rotating the sample to extinction.

Fluorescence Microscopy The custom-built fluorescence apparatus was based on a Nikon inverted microscope (model Eclipse TE2000) with a back-illuminated electron-multiplied EMCCD camera (model Cascade-II: 512, Photometrics, Inc.) for photon detection. Epi-illumination was provided by a metal halide lamp (model EXFO X-Cite 120, EXFO Lifesciences & Industrial Division) with exposure time adjusted by a computer-controlled Uniblitz shutter (model VMM-D3, Oz Optics Ltd.). The 10× magnification was provided by Nikon objective with a plan-Fluorite design, a NA of 0.30 and a working distance of 16.0 mm. Temperature was held constant using a Peltier-based heating and cooling stage (model TD60-STC20A, Instec Inc.) with a standalone temperature controller (model STC200, Instec Inc.). Metamorph 6.3 software (Molecular Imaging, Sunnyvale, Calif.) was used for the image acquisition/processing and shutter controls.

DNA Hybridization: For hybridization, a 16 mer target, GCACGAAGTTTTTTCT (SEQ ID NO: 2) (sequence A'), was dissolved in 5 mM sodium chloride solution to a concentration of 100 nM and added in a given amount to the chamber. The melting temperature (Tm) of this target to the ssDNA probe A was calculated to be 32.12° C. in bulk solution in the presence of 50 mM monovalent cations. The sample was held constant at 25° C. and observed with the polarizing or fluorescence microscope. Deionized water (resistivity=18.2 MΩ-cm) was added to keep the water level constant, as needed. 6-FAM labeled on the 5' end of the target (Operon) was used for the fluorescence experiments. For fluorescence microscopy experiments, the target DNA solution was exchanged for 5 mM NaCl solution following hybridization in order to reduce background fluorescence. Control experiments were performed with other 16 mers with various degrees of mismatch to probe A, including random, GGGCGGATGAGTCAGT (SEQ ID NO:3) (sequence B), two-base-pair mismatch (2 bpmm), GCAGGAAGTTTATTCT (SEQ ID NO:4) (Tm=13.15° C.) (using Oligo mismatch calculator), and one-base-pair mismatch (1 bpmm), GCACGAACTTTTTTCT (SEQ ID NO:5) (Tm=17.58° C.) (using Oligo mismatch calculator).

Results

Interactions between DNA and an adsorbed cationic surfactant monolayer at the nematic liquid crystal (LC)/aqueous interface were investigated using polarization microscopy to observe changes in LC anchoring. The adsorption of single-stranded DNA (ssDNA) to the hydrophilic headgroups of a cationic surfactant monolayer caused a two-dimensional (2D) phase transition within the monolayer that resulted in a reorientation of the nematic liquid crystal from homeotropic alignment (zero zenithal angle) to an intermediate tilt angle. The ssDNA was presumed to bind to the monolayer via electrostatic interactions between the cationic headgroups and anionic phosphate backbone of the DNA molecules, changing the structure of the monolayer. Subsequent exposure of the ssDNA/cationic surfactant monolayer complex to its ssDNA complement induced a second phase change characterized by the nucleation and growth of monolayer domains that caused homeotropic LC alignment. Fluorescence microscopy showed that the complement was co-localized in the same regions as the homeotropic domains. This second phase transition (also referred to herein as reorienting) did not occur upon exposure to non-complementary ssDNA, suggesting that DNA hybridization to the DNA/cationic complex triggered the 2D phase separation (also referred to herein as reorienting). This hybridization occurred at the interface despite the fact that the conditions in bulk solution were such that hybridization did not occur (high stringency), suggesting that the presence of the cationic surfactant monolayer neutralized electrostatic repulsion and allowed for hydrogen bonding between DNA complements. In addition to directly proving that a phase change may be brought about by a biorecognition event, such a system may be used for labelless and portable DNA detection. Indeed, LC response to ssDNA target was detected with a lower limit of 50 fmol of complement and was sufficiently selective to differentiate a one-base-pair mismatch in a 16 mer target.

Following the immersion of the LC-filled grids into aqueous solution, the initially birefringent grid holes (FIG. 1a) quickly became dark (homeotropic anchoring) as OTAB dissolved in the LC adsorbed and modified the structure of the nematic/aqueous interface (FIG. 1b). The steady-state surface coverage was directly correlated to the concentration of the surfactant in the LC layer. If ssDNA probes (A) were also included in the aqueous solution, the rapid change to homeotropic anchoring was followed by a slower process where birefringent regions appeared and grew (FIG. 1c). The birefringent domains displayed colors indicative of low effective birefringence (white, yellow, and orange in this case) with effective birefringence increasing as the birefringent domains continued to expand. Over the course of 30 minutes, the birefringent domains continued to form and merge until only small regions of homeotropic alignment remained (FIG. 1d). If no OTAB was dissolved in the LC, the ssDNA probe in solution had no effect on the alignment of the LC, the textures being analogous to that of pure water, i.e. azimuthall-disordered with high effective birefringence (FIG. 1a).

Figure 2:
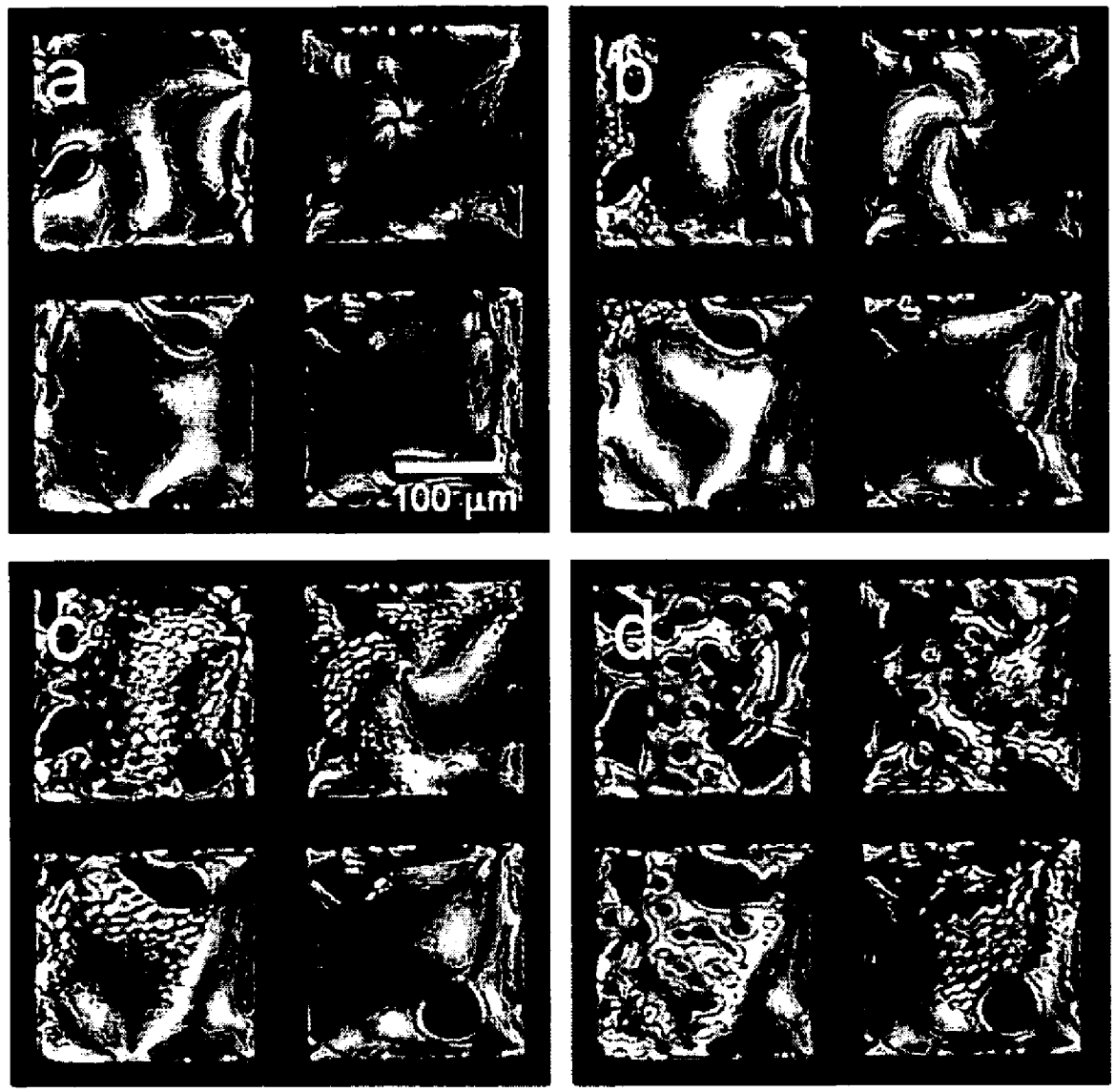
FIG. 2 illustrates hybridization of 1 pmol ssDNA target to an OTAB/ssDNA interfacial layer at the LC/aqueous interface; (a) No target; (b-d) Homeotropic domains appear and grow upon addition of complementary target.

The experimental arrangement described above permitted the direct observation of interfacial hybridization to a complementary target without additional preparation. In particular, it was not necessary to remove excess (un-adsorbed) ssDNA probe from solution because the solution conditions were of sufficiently high stringency as to inhibit bulk hybridization (Kelsee et al., 1996). Hybridization of 1 pmol target (A') to the OTAB/ssDNA monolayer (FIG. 2a) caused the sudden nucleation of small homeotropic domains in the LC (FIGS. 2b-d). Homeotropic domains often appeared in a matter of seconds for pmol amounts of target; the response time was slowed to the order of minutes for fmol amounts of target and for higher stringency conditions (i.e. addition of formamide as described below). The initially small homeotropic domains grew and coalesced, finally reaching a steady-state surface coverage of homeotropic alignment dependent on concentration of the target and conditions of the experiment.

The appearance of homeotropic regions was accompanied by a measurable increase in the birefringence of the remaining birefringent regions. For the case shown in FIG. 3, the increase of birefringence corresponds to an increase of the zenithal tilt angle from $36\pm9°$ (FIG. 3a) to $53\pm6°$ (FIG. 3b) measured relative to the surface normal.

Figure 4:
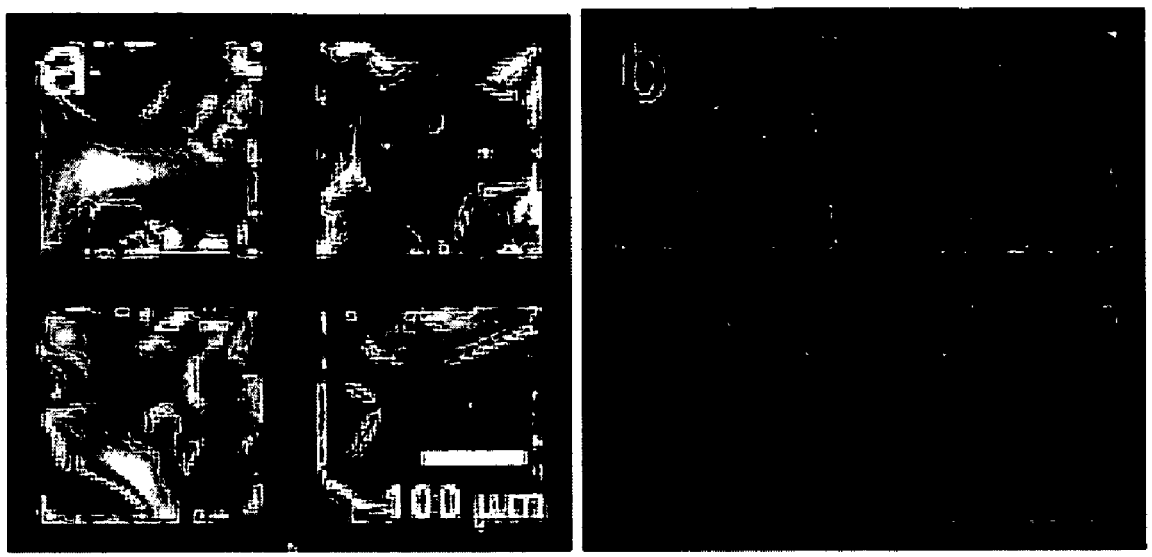
FIG. 4 illustrates domains following hybridization of 1 pmol labeled-ssDNA complementary target to an OTAB/ssDNA interfacial layer at the LC/aqueous interface; (a) Polarization microscopy (b) Fluorescence microscopy.
Figure 5:
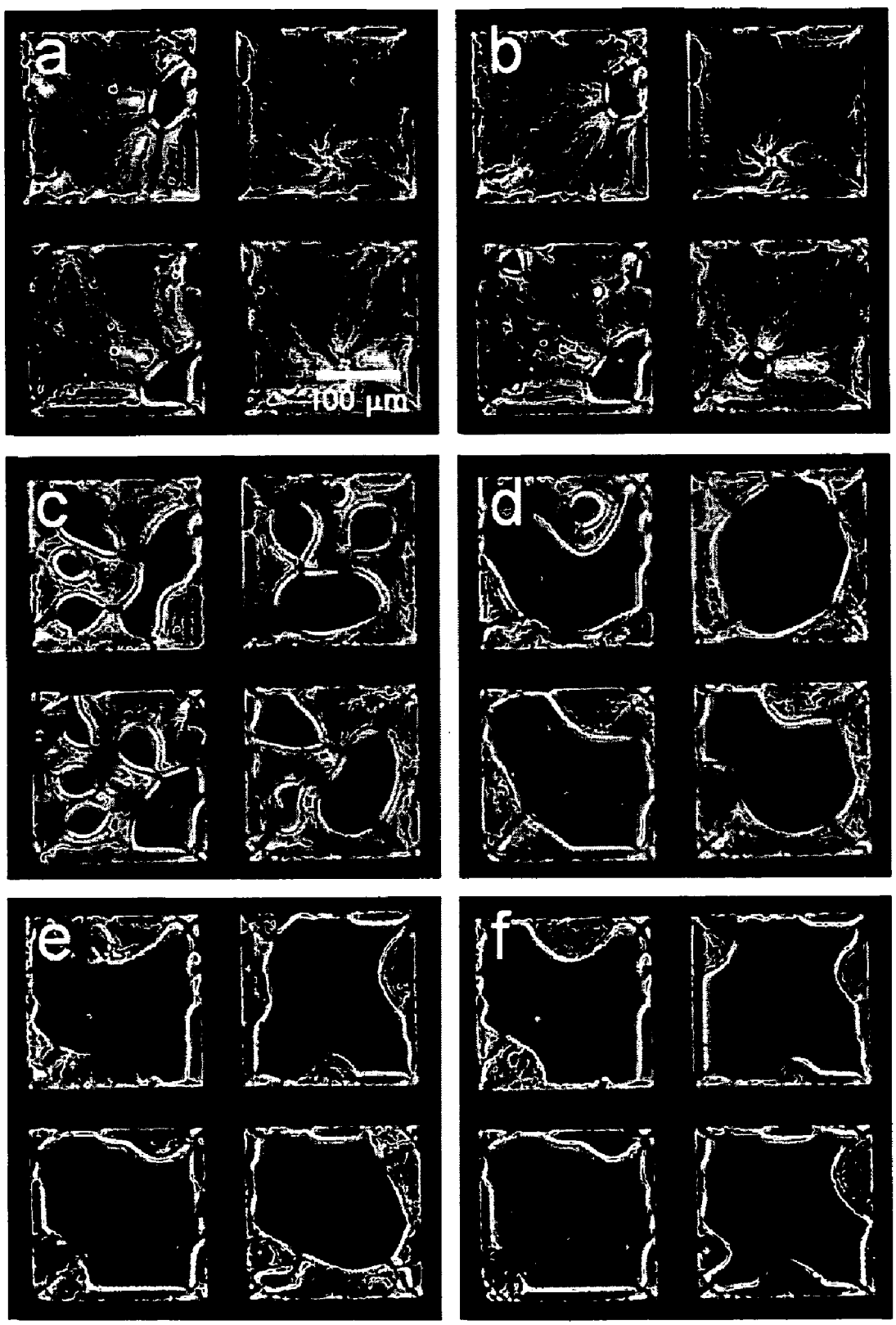
FIG. 5 illustrates the surface coverage of homeotropic domains upon binding to (a) 0, (b) 100 fmol, (c) 200 fmol, (d) 300 fmol, (e) 400 fmol, and (f) 500 fmol of target.

When fluorescently-labeled target DNA was used, a comparison of images obtained using fluorescence and polarization microscopy revealed a direct correspondence between LC domains and the concentration of the target at the interface (FIG. 4). In particular, the fluorescent ssDNA target was preferentially localized in the same lateral regions where the LC layer was homeotropically aligned. This established a direct relation between target binding at the interface and LC alignment.

FIGS. 5a-f show the LC response to incremental additions of 100 fmol target. The limit of detection was ~50 fmol, with measurable homeotropic domains observed for 100 fmol target. Between 50 and 400 fmol target, there was a dramatic response to the target causing a significant increase in coverage by homeotropic regions for each 50-100-fmol addition. The response saturated at ~500 fmol target with additional target causing no increase in homeotropic coverage. As expected, the response time of the system was affected by sample volume. In particular, sample volumes>500 μL resulted in noticeably slower kinetics limited by diffusive transport of target to the interface and decreased chemical potential of the bulk.

Figure 6:
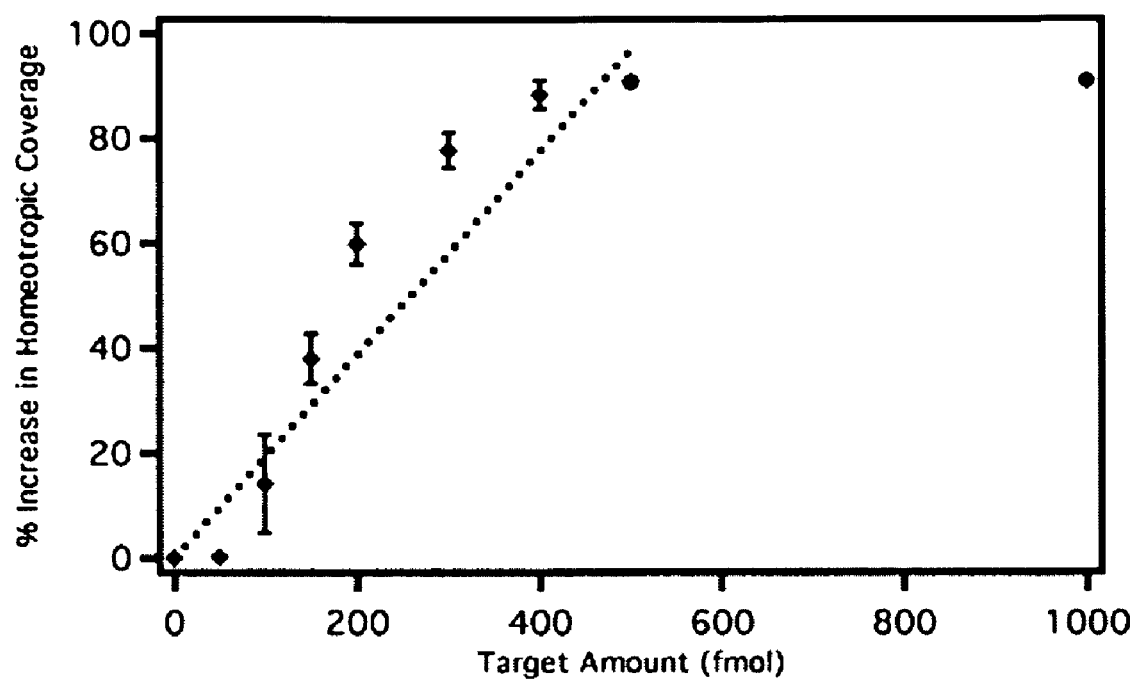
FIG. 6 illustrates dose-response curve for hybridization to the target wherein the dotted line represents the calculated close-packed area fraction of dsDNA assuming the interfacial hybridization of all target DNA as described below.

The LC response to ssDNA target was quantified by measuring the increase of the area fraction of homeotropic regions above the baseline prior to target addition. The dynamic response of the LC to target, FIG. 6, was an S-curve typical for sensor response showing the limit of detection (~50 fmol), dynamic range (100-500 fmol), and saturation of the response.

Figure 7:
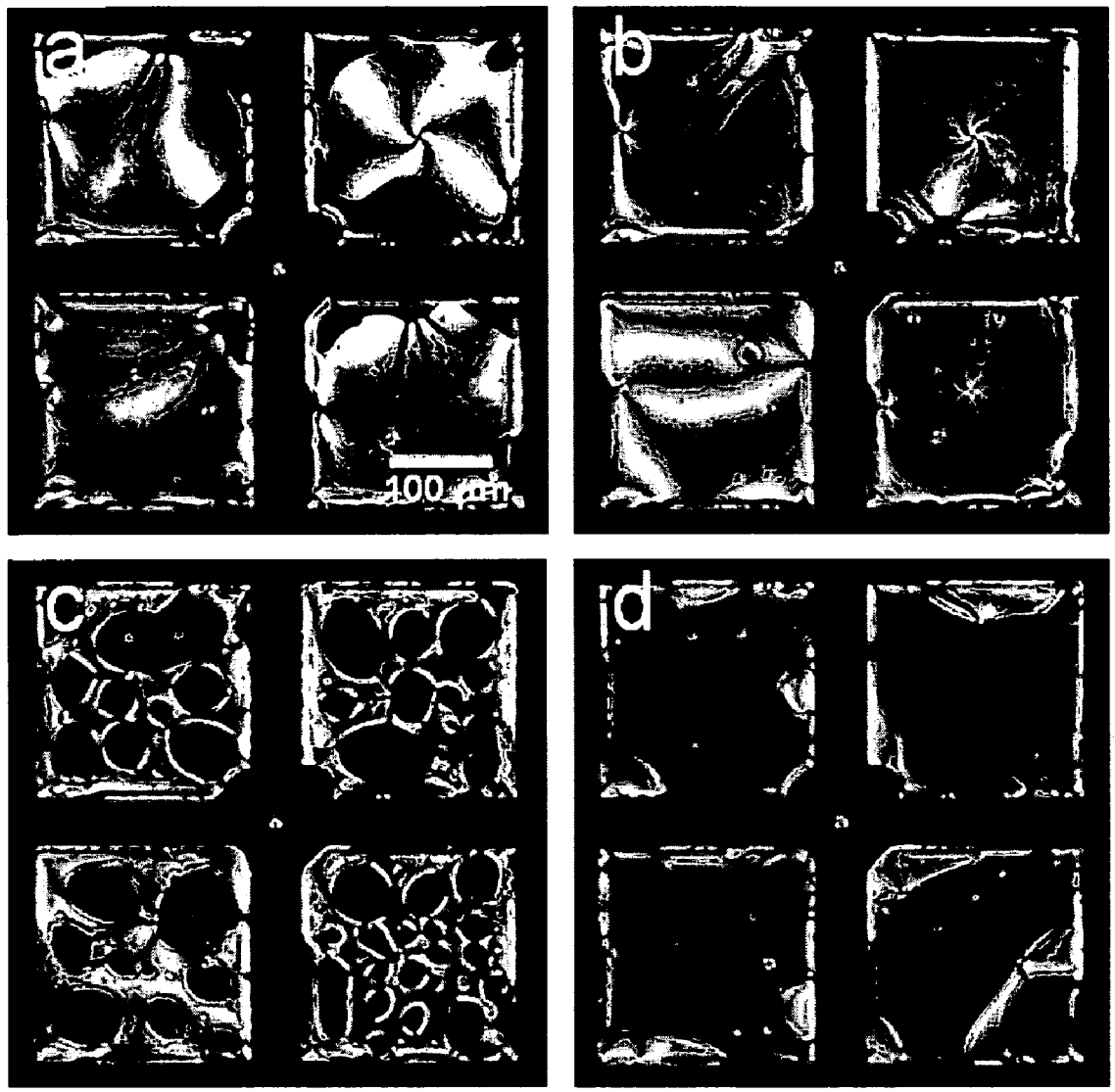
FIG. 7 illustrates LC response to 16 mer target, A', or 16 mer random sequence, B; (a) OTAB/A layer at the LC/aqueous interface; (b) 25 pmol B; (c) 25 pmol B+25 pmol A', 30 seconds after addition of A'; (d) 25 pmol B+25 pmol A', 25 minutes after addition of A'.

The LC response to the DNA target was sensitive to base pair mismatches in the 16 mer targets. As an initial control, a random 16 mer (B) was investigated that was not expected to hybridize to the monolayer probe (A), even under highly favorable conditions. An excess of B was used to highlight the specificity of the response even for relatively large amounts of the mismatch. FIG. 7a shows LC appearance following formation of an OTAB/ssDNA (A) interfacial layer. Addition of 25 pmols B caused the birefringence to increase slightly (consistent with the increase in birefringence observed by increased amounts of probe) but no homeotropic domains were observed to form (FIG. 7b). 25 pmols of the complementary target, A', were then added to solution. FIGS. 7c and 7d show the LC response 30 seconds and 25 minutes following the addition of A'; the formation and coalescence of homeotropic domains was clearly observed. An identical experiment using B as the interfacial probe (not shown) responded similarly to its target, B', demonstrating that response is independent of the oligonucleotide sequence.

Figure 8:
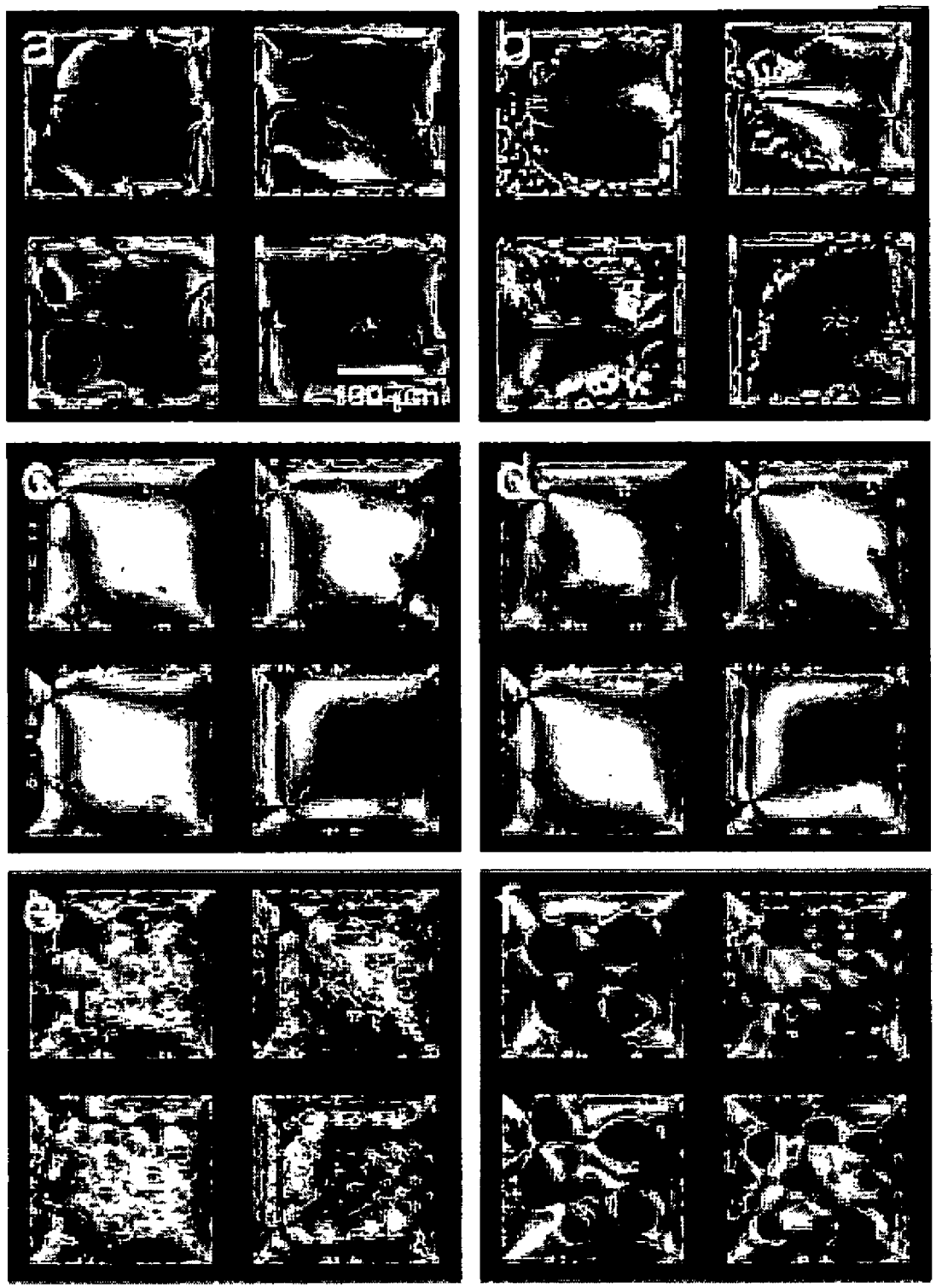
FIG. 8 illustrates LC response to 16 mer target, A', or 16 mer 1 bpmm; (a) OTAB/A layer adsorbed at the LC/aqueous interface; (b) 50 pmol 1 bpmm; (c) OTAB/A layer adsorbed at the LC/aqueous interface with 8% formamide; (d) 50 pmol 1 bpmm; (e) 50 pmol 1 bpmm+50 pmol A', 1 minute after addition of A'; (f) 50 pmol 1 bpmm+50 pmol A', 3 minutes after addition of A'.

A two base-pair-mismatch (2 bpmm, Tm=13.15° C.) in 16 was enough to completely prevent a LC response for the conditions described above (25° C., 5 mM NaCl). In this case, the LC response was similar to that of the random sequence, B. Specifically, the birefringence increased slightly when 50 pmol 2 bpmm was added but no homeotropic domains appeared. For 50 pmol of a one-base-pair mismatch (1 bpmm, Tm=17.58° C.) small homeotropic domains were observed to form near the edges of the grid holes (FIGS. 8a-b). Though significant, this response was dramatically decreased compared to a perfect match, which would have resulted in ~90% homeotropic coverage. The inclusion of 8% formamide to the aqueous phase increased the stringency of the system by effectively lowering the melting temperature ~6.0° C. and inhibited formation of homeotropic domains for 50 pmol of 1 bpmm (FIGS. 8c-d). Subsequent addition of 50 pmol target, A', caused the appearance, FIG. 8e, and coalescence, FIG. 8f, of homeotropic domains until 75-95% surface coverage by the homeotropic domains (not shown).

Discussion

Insight into the monolayer structure may be gained by comparing to analogous monolayers at different interfaces (Price et al., 2007). The air/water interface has been studied most often (Sastry et al., 2000; Symietz et al., 2004; Erpkhina et al., 2007) though other interfacial studies exist (Sastry et al., 2001). We will limit our discussion to cationic/DNA complexes at the air/water interface to compare with our results at the nematic LC/aqueous interface.

Past studies have shown that the adsorption and self-assembly of surfactant molecules at the interface between a liquid crystal and aqueous phase can modify the anchoring of the LC layer. (Price et al., 2007; Brake et al., 2005). These studies suggested, in fact, that amphiphilic monolayers can form at this interface in analogy with those known to form at the air/water and oil/water interfaces, and that these monolayers can adopt various 2D phases as a function of thermodynamic conditions (Kaganer et al., 1999). Different phases have different LC anchoring properties. In particular, very dilute phases often result in tilted anchoring, while denser monolayers often result in homeotropic anchoring. Similarly, self-assembled monolayers deposited on solid surfaces also control LC anchoring, with thicker, well-organized monolayers inducing homeotropic anchoring, and thinner, more dilute monolayers inducing tilted/planar anchoring. (Jerome et al., 1991) Molecular tilt within the surface layer may also influence LC anchoring; however, tilt is generally coupled to surface concentration in these systems.

In the current studies, the association between an adsorbed OTAB and ssDNA in solution reorganized the structure of the surfactant-laden interface (FIG. 1) causing a transition from homeotropic anchoring to tilted.

In the current studies, the association between adsorbed OTAB and ssDNA in solution reorganized the structure of the surfactant-laden interface (FIG. 1) causing a transition from homeotropic anchoring to tilted. Previous studies involving ssDNA interactions with Langmuir monolayers of cationic surfactant (octadecylamine, ODA; or cetyltrimethylammonium bromide, CTAB) indicated that an interfacial complex forms due to electrostatic interactions (Sastry, M. et al., 2000; Erokhina, S. et al., 2007; Nicolini, C. et al., 1997) and that surface-pressure versus area isotherms of the complex are shifted to larger molecular areas relative to the pure surfactant. Sastry, M. et al., 2000. Without being bound by any particular mechanistic theory, it is believe that the interaction of ssDNA with the adsorbed surfactant induces a subtle change in the structure of the surfactant layer (without a dramatic change in average interfacial concentration) inducing a change in LC anchoring. These studies show that the cationic surfactant interface provides a local environment conducive to DNA hybridization.

Once tilted anchoring was induced by addition of ssDNA, additional ssDNA did not qualitatively change the structure of the interface. However, the addition of even small amounts of complement caused a significant LC response. As observed in FIGS. 2 and 5, femtomole additions of the complementary ssDNA target caused nucleation, growth, and coalescence of LC homeotropic domains. Fluorescence experiments (FIG. 4) confirmed that these homeotropic domains correspond to areas where the target accumulated at the interface. As discussed above, homeotropic anchoring is often associated with a concentrated surfactant layer.

Figure 3:
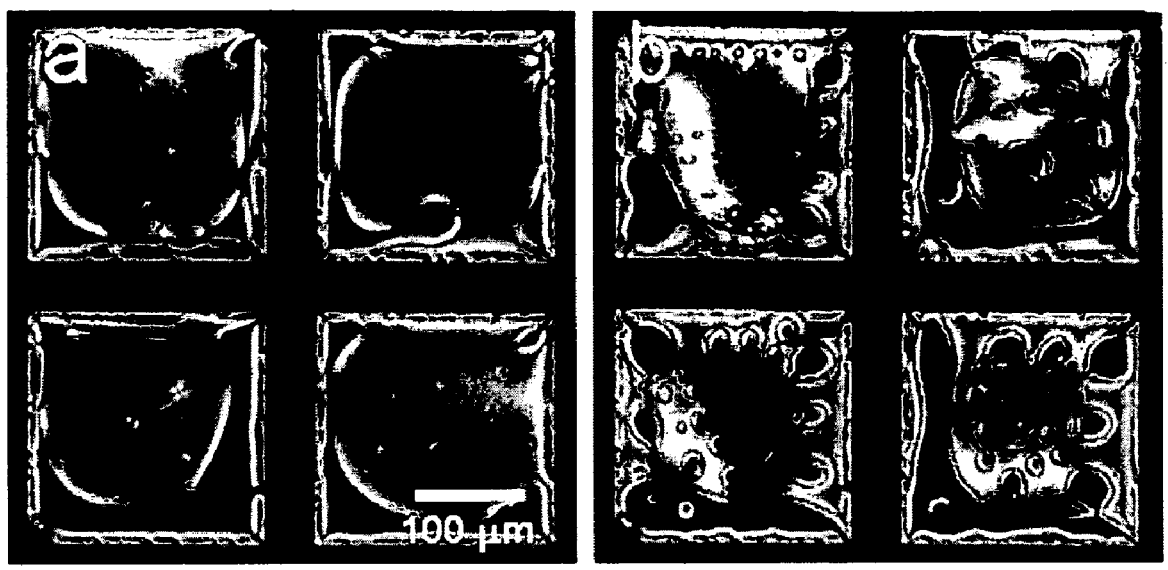
FIG. 3 illustrates the nucleation of homeotropic domains causing the zenithal tilt angle in the SmC-like phase to increase as indicated by the rise in birefringence, i.e. zenithal tilt increases from (a) 28°-45° to (b) 47°-58°.

To put the sensitivity of the LC response into a molecular context, it is instructive to estimate the average surface density of dsDNA within the homeotropic regions. An upper limit can be calculated by assuming that all target in solution hybridizes to probe at the interface with no molecules overlapping or extending into the solution. For B-DNA, the most common helical form, the helix length is 0.34 nm/base pair with a diameter of 2.37 nm.40 Assuming a flat-lying molecular orientation, these dimensions project an area of 12.9 nm2/molecule. So for 50 fmol, the limit of detection, the maximum area occupied is 0.39 mm2, while for 500 fmol, the saturation of LC response, the maximum area is 3.9 mm2. The open area in the TEM grid is approximately 4.0 mm2, so the calculated upper limit of DNA surface coverage is 10% and 100% for 50 fmol and 500 fmol of target respectively as indicated by the dotted line in FIG. 6. Notably, these values increase over the same range of target measured experimentally. While this should be regarded only as an order-of-magnitude estimate, it is consistent with the first-order approximation that the amount of homeotropic region created may be directly related to the area occupied by a relatively close-packed layer of dsDNA associated with the surfactant-laden interface. It is also noted that the nucleation of homeotropic domains is accompanied by an increase in birefringence, and therefore LC tilt angle, in the coexisting birefringent region (FIG. 3).

In sum, polarization microscopy was used to observe LC anchoring coupled to structural changes of a cationic surfactant-laden interface upon interaction with ssDNA and subsequent hybridization to complementary ssDNA. The association of a ssDNA probe and the interface caused a structural change that reoriented the adjacent nematic LC from homeotropic to tilted alignment. The subsequent hybridization of complementary target ssDNA to the ssDNA/surfactant interfacial complex resulted in the nucleation of homeotropic domains, possibly due to the emergence of interfacial regions where the surfactant/DNA complex was condensed. Fluorescence microscopy confirmed that the ssDNA target was co-localized in the same regions as these homeotropic domains. The high stringency conditions of the bulk aqueous phase (low ionic strength) largely confined the hybridization reaction to the interface where the cationic surfactant neutralized the electrostatic repulsion between the probe and target. The sensitivity of the LC anchoring to the interfacial structure allowed for the detection of DNA 16 mers with a lower limit of ~50 fmol and the ability to differentiate a one-base-pair mismatch between the probe and target.

BIBLIOGRAPHY

Brake, J. M., and Abbott, N. L. (2007), Langmuir, 23, 8491-507

Park, J.-S., Teren, S., Tepp, W. H., Beebe, D. J., Johnson, E. A., and Abbott, N. L. (2006), Chem. Mater., 18, 6147-6151.

Clare, B. H., and Abbott, N. L. (2005), Langmuir, 21, 6451-6461.

Kim, H.-R., Kim, J.-H., Kim, T.-S., Oh, S.-W., and Choi, E.-Y. (2005), Appl. Phys. Lett., 87, 143901.

Brake, J. M., Daschner, M. K., Luk, Y.-Y., and Abbott, N. L. (2003), Science, 302, 2094-2097.

Luk, Y.-Y., Tingey, M. L., Hall, D. J., Israel, B. A., Murphy, C. J., Bertics, P. J., and Abbott, N. L. (2003), Langmuir, 19, 1671-1680.

Kim, S.-R., and Abbott, N. L. (2002), Langmuir, 18, 5269-5276.

Gupta, V. K., Skaife, J. J., Dubrovsky, T. B., and Abbott, N. L. (1998), Science, 279, 2077-2080.

Hoogboom, J., Clerx, J., Otten, M. B. J., Rowan, A. E., Rasing, T. and Nolte, M. (2003), Chem. Commun., 2856-2857.

Blum, L. J. and Coulet, P. R. (1991), in Biosensor Principles and Applications, (Marcel Dekker, New York).

de Gennes, P. J. and Prost, J. (1995), in The Physics of Liquid Crystals, 2nd ed., (Oxford University Press, New York).

Dunmur, D., Fukuda, A. and Luckhurst, G. R. (2001), in Physical Properties of Liquid Crystals: Nematics, (INSPEC, Institution of Electrical Engineers, London).

Rasing, T. and Musevic, I. (2004), in Surfaces and Interfaces of Liquid Crystals (Springer, Berlin).

Price, A. D. and Schwartz, D. K. (2007), J. Phys. Chem. B, 111, 1007-1015.

Lockwood, N. A., and Abbott, N. L. (2005), Curr. Opin. Colloid Interface Sci, 10, 111-120.

Brake, J. M., Daschner, M. K., and Abbott, N. L. (2005), Langmuir, 21, 2218-2228.

Kaganer, V. M., Mohwald, H. and Dutta, P. (1999), Rev. Mod. Phys., 71, 779-819.

Brake, J. M., Mezera, A. D., and Abbott, N. L. (2003), Langmuir, 19, 6436-6442.

Osica, V. D., Pyatigorskaya, T. L., Polyvtsev, O. F., Dembo, A. T. Kliya, M. O., Vasilchenko, V. N., Verkin B. I., and Sukharevsky, B. Y. (1977), Nucleic Acids Res., 4, 1083-1096.

Radler, J. O, Koltover, I., Salditt, T., and Safinya, C. R. (1997), Science, 275, 810-814.

Koltover, I., Salditt, T., Radler, J. O., and Safinya, C. R. (1998), Science, 281, 78-81.

Miller, A. D. (1998), Angew. Chem. Int. Ed., 37, 1768-1785.

Sastry, M., Ramakrishnan, V., Pattarkine, M., Gole, A., and Ganesh, K. N. (2000), Langmuir, 16, 9142-9146.

Erokhina, S., Berzina, T., Cristofolini, L., Konovalov, O., Erokhin V., and Fontana, M. P. (2007), Langmuir, 23, 4414-4420.

Sukhorukov, G. B., Montrel, M. M., Retrov, A. I., Shabarchina, L. I., and Sukhorukov, B. I. (1996), Biosens. Bioelectron., 11, 913-922.

Kago, K., Matsuoka, H., Yoshitome, R., Yamaoka, H., Ijiro, K., and Shimomura, M. (1999), Langmuir, 15, 5193-5196.

Ramakrishnan, V., Costa, M. D., Ganesh, K., and Sastry, M. (2004), J. Colloid Interf. Sci., 276, 77-84.

Symietz, C., Schneider, M., Brezesinski, G., and Mohwald, H. (2004), Macromolecules, 37, 3865-3873.

Cardenas, M., Nylander, T., Jonsson, B., and Lindman, B. (2005), J. Colloid Interf. Sci., 286, 166-175.

Chen, X., Wang, J., and Liu, M. (2005), J. Colloid Interf. Sci., 287, 185-190.

Walba, D. M., Liberko, C. A., Korblova, E., Farrow, M., Furtak, T. E., Chow, B. C., Schwartz, D. K., Freeman, A. S., Douglas, K., Williams, S. D., et al. (2004), Liq. Cryst., 31, 481-489.

Robinson, P. C. and Davidson, M. W. (2006) Michel-Levy Interference Color Chart (http://www.microscopyu.com/articles/polarized/michel-levy.html).

Kelsee, R. E. in, Basic DNA and RNA Protocols, ed Harwood, A. J. (Humana Press, Totowa, N.J.), pp 31-39.

Sastry, M., Kumar, A., Pattarkine, M., Ramakrishnan, V., and Ganesh, K. N. (2001), Chem. Commun., 1434-1435.

Crusats, J., Albalat, R., Claret, J. Ignes-Mullol, J., and Sagues, F. (2004), Langmuir, 20, 8668-8674.

Voet, D.; Voet, J. G.; Pratt, C. W. (2006) in, Fundamental of Biochemistry: Life at the Molecular Level} (Wiley, New York).

Nicolini, C., Erokhin V., Facci, P., Guerzoni, S., Ross, A., and Paschkevitsch, P. (1997), Biosens. Bioelectron., 12, 613-618.

Batel, R., Jaksic, Z., Bihari, N., Hamer, B., Fafandel, M., Chauvin C., Schroder, H. C., Muller, W. E. G., and Zahn, R. K. (1999), Anal. Biochem., 270, 195-200.

Ganesh, K. N. and Sastry, M. (2002), J. Indian Inst. Sci., 82, 105-112.

Jérôme, B. Rep. Prog. Phys. 1991, 54, 391-451.

What is claimed is:

1. A method of detecting hybridization of a probe nucleic acid and a sample nucleic acid, said method comprising the steps of:
   i. contacting a sample nucleic acid with a cationic surfactant-nucleic acid interfacial layer, wherein said cationic surfactant-nucleic acid interfacial layer comprises a cationic surfactant and a probe nucleic acid, and said cationic surfactant-nucleic acid interfacial layer is present at the interface of a liquid crystal and a polar solvent;
   ii. allowing said sample nucleic acid to hybridize to said probe nucleic acid thereby reorienting said liquid crystal; and
   iii. detecting said reorienting thereby detecting hybridization of said probe nucleic acid to said sample nucleic acid.

2. The method of claim 1, wherein said probe nucleic acid and said sample nucleic acid are DNA or RNA.

3. The method of claim 1, wherein the probe nucleic acid is from 5 to 50 nucleobases in length.

4. The method of claim 1, wherein the probe nucleic acid is from 20 to 30 nucleobases in length.

5. The method of claim 1, wherein said cationic surfactant is a monoalkylquaternary ammonium surfactant, dialkylquaternary ammonium surfactant, trialkylquaternary ammonium surfactant, or a monoalkylpyridinium surfactants.

6. The method of claim 1, wherein said cationic surfactant is a monoalkylquaternary ammonium salt.

7. The method of claim 1, wherein said liquid crystal is a thermotropic liquid crystal.

8. The method of claim 1, wherein said liquid crystal is 5CB (4-Cyano-4'-pentylbiphenyl), 5CT (4-Cyano-4'-pentyl-p-terphenyl), MBBA (N-(4-methoxybenzylidene-4'-butylaniline), 4'-Di-n-hexyldiphenyldiacetylene, or a mixture thereof.

9. The method of claim 1, wherein said detecting said reorienting comprises detecting a change in the birefringence of said liquid crystal.

10. The method of claim 1, wherein said detecting comprises detecting a change in polarization of light emanating from said liquid crystal.

11. The method of claim 1, where said polarization is measured using light microscopy.

12. The method of claim 1, where said polar solvent is an aqueous solution.

* * * * *